US010688047B2

(12) United States Patent
Colombo et al.

(10) Patent No.: US 10,688,047 B2
(45) Date of Patent: Jun. 23, 2020

(54) PHYSICALLY AND CHEMICALLY STABLE ORAL SUSPENSIONS OF GIVINOSTAT

(71) Applicant: ITALFARMACO SPA, Milan (IT)

(72) Inventors: Giuseppe Colombo, Seregno (IT); Roberta Artico, Milan (IT); Paolo Mascagni, Alicante (ES); Maria Valmen Monzani, Milan (IT); Silvia Puccianti, Corbetta (IT)

(73) Assignee: ITALFARMACO SPA, Milan (IT)

(*) Notice: Subject to any disclaimer, the term of this patent is extended or adjusted under 35 U.S.C. 154(b) by 0 days.

(21) Appl. No.: 15/770,443

(22) PCT Filed: Oct. 28, 2016

(86) PCT No.: PCT/IB2016/056496
§ 371 (c)(1),
(2) Date: Apr. 23, 2018

(87) PCT Pub. No.: WO2017/077436
PCT Pub. Date: May 11, 2017

(65) Prior Publication Data
US 2018/0311160 A1 Nov. 1, 2018

(30) Foreign Application Priority Data
Nov. 3, 2015 (IT) .................. 102015000068150

(51) Int. Cl.
A61K 9/00 (2006.01)
A61K 47/10 (2017.01)
A61K 9/10 (2006.01)
A61K 47/26 (2006.01)
A61K 31/167 (2006.01)
A61P 7/02 (2006.01)
A61P 21/00 (2006.01)
A61P 19/02 (2006.01)
A61P 35/02 (2006.01)
A61K 31/325 (2006.01)
A61K 47/02 (2006.01)
A61K 47/12 (2006.01)
A61K 47/36 (2006.01)

(52) U.S. Cl.
CPC ............ *A61K 9/10* (2013.01); *A61K 9/0053* (2013.01); *A61K 9/0095* (2013.01); *A61K 31/167* (2013.01); *A61K 31/325* (2013.01); *A61K 47/02* (2013.01); *A61K 47/10* (2013.01); *A61K 47/12* (2013.01); *A61K 47/26* (2013.01); *A61K 47/36* (2013.01); *A61P 7/02* (2018.01); *A61P 19/02* (2018.01); *A61P 21/00* (2018.01); *A61P 35/02* (2018.01)

(58) Field of Classification Search
None
See application file for complete search history.

(56) References Cited

U.S. PATENT DOCUMENTS

| 4,169,150 A * | 9/1979 | Hara ................. C07D 209/48 514/220 |
| 5,023,257 A * | 6/1991 | Pollinger ............ A61K 9/0019 514/224.5 |
| 5,695,784 A * | 12/1997 | Pollinger ............ A61K 9/0095 424/489 |
| 2009/0111872 A1* | 4/2009 | Embrechts .......... A61K 9/0095 514/489 |
| 2011/0105536 A1* | 5/2011 | Lewyn-Briscoe ... A61K 31/519 514/259.41 |
| 2012/0039953 A1* | 2/2012 | Artico ................. A61K 9/0095 424/400 |

FOREIGN PATENT DOCUMENTS

| EP | 0847992 B1 | 6/2004 |
| WO | 93/07148 A1 | 4/1993 |
| WO | 97/43251 A1 | 11/1997 |
| WO | 02/22577 A2 | 3/2002 |
| WO | 02/30879 A2 | 4/2002 |
| WO | 03/076422 A1 | 9/2003 |
| WO | 2004/065355 A1 | 8/2004 |
| WO | 2004/069823 A1 | 8/2004 |
| WO | 2004/071400 A2 | 8/2004 |
| WO | 2004/092115 A2 | 10/2004 |
| WO | 2005/019174 A1 | 3/2005 |
| WO | 2006/003068 A2 | 1/2006 |
| WO | 2006/010750 A1 | 2/2006 |
| WO | 2006/018814 A2 | 2/2006 |
| WO | WO2007135362 * | 11/2007 |

(Continued)

OTHER PUBLICATIONS

Chen et al. Investigation of the Preparation and Stability of Vorinostat Capsule, <<China Pharmacy>> 2013-33 (Year: 2013).*
International Search Report dated Jan. 30, 2017 for International Application No. PCT/162016/056496.
Adcock, "HDAC inhibitors as anti-inflammatory agents", British Journal of Pharmacology (2007) 150, Feb. 26, 2007, pp. 829-831.
Bi, et al., "The Molecular Mechanism of HDAC Inhibitors in Anticancer Effects", Cellular & Molecular Immunology, vol. 3 No. 4, Aug. 2006, pp. 285-290.
Blanchard, et al., "Histone deacetylase inhibitors: new drugs for the treatment of inflammatory diseases?", Drug Discovery Today, vol. 10, No. 3, Feb. 2005, pp. 197-204.
Leoni, et al., "The Histone Deacetylase Inhibitor ITF2357 Reduces Production of Pro-Inflammatory Cytokines In Vitro and Systemic Inflammation In Vivo", Molecular Medicine, vol. 11, No. 1-12, Jan.-Dec. 2005, pp. 1-15.

(Continued)

Primary Examiner — Jennifer A Berrios
(74) Attorney, Agent, or Firm — Hueschen and Sage

(57) ABSTRACT

Physically and chemically stable oral liquid formulations of Givinostat (Diethyl-[6-(4-hydroxycarbamoyl-phenylcarbamoyloxymethyl)-naphthalen-2-yl-methyl]-ammonium chloride) are disclosed, together with methods for the preparation thereof. Such oral formulations are in the form of aqueous suspensions and contain Givinostat and/or pharmaceutically acceptable salts and/or derivatives thereof, at least a wetting agent and/or at least a density-imparting agent. Such formulations are suitable for oral administration for systemic therapeutic action.

17 Claims, No Drawings

(56) References Cited

FOREIGN PATENT DOCUMENTS

| WO | 2008/033747 A2 | | 3/2008 |
|---|---|---|---|
| WO | 2011/113013 A2 | | 9/2011 |
| WO | 2013/114413 A1 | | 8/2013 |
| WO | 2013114413 A1 | | 8/2013 |
| WO | 2014159224 A1 | | 10/2014 |
| WO | WO2014165226 | * | 10/2014 |
| WO | WO WO2015086738 | | 6/2015 |

OTHER PUBLICATIONS

Lieberman, et al., "Pharmaceutical Dosage Forms, Disperse Systems", Marcel Dekker, New York and Basel, vol. 1, 1988.
Stahl, et al., "Handbook of Pharmaceutical Salts—Properties, Selection, and Use", Wiley-VCH, 127-133, 2008.
R. Christian Moreton, "Commonly Used Excipients in Pharmaceutical Suspensions", Pharmaceutical Suspensions, Springer, 2010, p. 67-102.

* cited by examiner

PHYSICALLY AND CHEMICALLY STABLE ORAL SUSPENSIONS OF GIVINOSTAT

This application is a National Stage of International Application PCT/IB2016/056496, filed Oct. 28, 2016, published May 11, 2017, under PCT Article 21(2) in English; which claims the priority of Italian Application No. 102015000068150, filed Nov. 3, 2015. The contents of the above-identified applications are incorporated herein by reference in their entireties.

The present invention relates to physically and chemically stable formulations of Givinostat and/or pharmaceutically acceptable salts and/or derivatives thereof suitable for oral administration.

BACKGROUND OF THE INVENTION

Histone deacetylases (HDAC) are a class of enzymes that remove acetyl groups from an ε-N-acetyl lysine amino acid on a histone. This is important because DNA is wrapped around histones, and DNA expression is regulated by acetylation and de-acetylation.

HDAC inhibitors (HDACi) have effects on non-histone proteins that are related to acetylation. HDACi can alter the degree of acetylation of these molecules and, therefore, increase or repress their activity. HDACi have a long history of use in psychiatry and neurology as mood stabilizers and anti-epileptics, for example Valproic acid. In more recent times, they are being studied as antineoplastic and anti-inflammatory drugs.

In tumor cells, HDACi inhibit cell proliferation and induce cell death and differentiation [Gaofeng Bi and Guosheng Jiang in *Cellular & Molecular Immunology* 3, 285-290 (2006)].

Histone deacetylase inhibitors are also capable of modulating the production of cytokines and other pro-inflammatory factors on the part of immuno-competent cells and have demonstrated, in vivo, anti-inflammatory properties [Frederic Blanchard and Celine Chipoy in *Drug Discovery Today* 10, 197-204 (2005); IM Adcock in *British Journal of Pharmacology* 150, 829-831(2007)].

Some of the histone deacetylase inhibitors currently at the clinical study stage are described, with other analogues thereof, in the following patents: WO 2004/092115, WO 2005/019174, WO 2003/076422, WO 2006/010750, WO 2006/003068. WO 2002/030879, WO 2002/022577, WO 1993/007148, WO 2008/033747. WO 2004/069823, EP 0847992 and WO 2004/071400, the contents of which are incorporated herein by reference in their entirety.

Recently, a histone deacetylase inhibitor (Zolinza, Vorinostat) has been approved for the treatment of cutaneous T-cell lymphoma. Zolinza is in the form of capsule and is administered orally.

Givinostat (originally referred to as ITF2357) is described in WO 97/43251 (anhydrous form) and in WO 2004/065355 (monohydrate crystal form), herein both incorporated by reference. WO 2013/114413 describes the use of Givinostat for treating muscular dystrophy. Givinostat is an orally active histone deacetylase inhibitor.

In lipopolysaccharide (LPS)-stimulated cultured human peripheral blood mononuclear cells (PBMCs), ITF2357 reduces by 50% the release of tumor necrosis factor-α (TNFα) at concentration of 10 to 22 nM, the release of intracellular interleukin IL-1β at 12 nM, the secretion of IL-1β at 12.5 to 25 nM, and the production of interferon-γ (IFNγ) at 25 nM. Oral administration of 1.0 to 10 mg/kg ITF2357 to mice reduced LPS-induced serum TNFα and IFNγ by more than 50% [Flavio Leoni et al. in *Molecular Medicine* 11, 1-15 (2005)].

Givinostat is in numerous phase II clinical trials (including for relapsed leukemias and myelomas), and has been granted orphan drug designation in the European Union for the treatment of systemic juvenile idiopathic arthritis and polycythaemia vera and more recently for treatment of Duchenne muscular dystrophy. It is being used either alone or in combination with other drugs.

Solid dosage formulations are the commonest forms intended for oral administration of a drug. In spite of the numerous advantages they offer, many patients complain that it is difficult for them to take some currently used dosage forms such as tablets, capsules, or powders, due to difficulties in swallowing. This is particularly true for elderly and pediatric patients. In addition, patients on chemotherapy treatment may have nausea and emesis, which complicates the administration of conventional tablets and capsules.

WO 2004/092115, WO 2005/019174, and WO 2003/076422 describe histone deacetlase inhibitors that can be administered as pharmaceutical compositions by any of the following routes: oral, systemic (e.g., transdermal, intranasal or rectal), or parenteral administration, preferably administered by oral or parenteral route. However, in no cases, specific formulation aspects of oral suspension formulations are addressed, nor any manufacturing description of such formulations is given.

In particular, in the prior art, no specific formulation aspects of Givinostat oral suspension formulations are reported, nor any manufacturing description of such formulations is given.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

Within the framework of the present description and in the subsequent claims, except where otherwise indicated, all numbers expressing amounts, quantities, percentages, and so forth, are to be understood as being preceded in all instances by the term "about". Also, all ranges of numerical entities include all the possible combinations of the maximum and minimum numerical values and all the possible intermediate ranges therein, in addition to those specifically indicated hereafter.

The term "physiologically acceptable excipient" herein refers to a substance devoid of any pharmacological effect of its own and which does not produce adverse reactions when administered to a mammal, preferably a human. Physiologically acceptable excipients are well know-n in the art and are disclosed, for instance in the *Handbook of Pharmaceutical Excipients, sixth edition* (2009), herein incorporated by reference.

The term "Pharmaceutically acceptable salts or derivatives" herein refers to those salts or derivatives which possess the biological effectiveness and properties of the salified or derivatized compound and which and which do not produce adverse reactions when administered to a mammal, preferably a human. The pharmaceutically acceptable salts may be inorganic or organic salts; examples of pharmaceutically acceptable salts include but are not limited to: carbonate, hydrochloride, hydrobromide, sulphate, hydrogen sulphate, citrate, maleate, fumarate, trifluoroacetate, 2-naphthalenesulphonate, and para-toluenesulphonate. Further information on pharmaceutically acceptable salts can be found in *Handbook of pharmaceutical salts*, P. Stahl, C. Wermuth, *WILEY-VCH*, 127-133, 2008, herein incorporated by reference. The pharmaceutically acceptable derivatives include the esters, the ethers and the N-oxides.

The terms "comprising", "having", "including" and "containing" are to be construed open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as semi-closed terms, meaning that no other ingredients which materially affects the basic and novel characteristics of the invention are included (optional excipients may thus included).

The terms "consists of", "consisting of" are to be construed as closed terms.

For the purposes of the present invention, the expression "w/v" is intended to indicate the weight of the mentioned compound (in g) with respect to the volume of the whole suspension (per 100 mL).

For the purposes of the present invention, with the term "wetting agent" is intended to indicate a substance that promotes proper wetting of a hydrophobic material, for example, by reducing the interfacial tension and contact angle between the solid particles and liquid carrier, as for instance disclosed in "Pharmaceutical Dosage Forms, Disperse Systems", Volume 1, edited by H. A. Lieberman, M. M. Rieger, and G. S. Banker, 1988 by Marcel Dekker, New York and Basel.

For the purposes of the present invention, the term "suspending agent" is intended to indicate a substance that imparts viscosity and/or acts as a protective colloid, thus resulting in a stable dispersion, in that they retard settling and agglomeration of the particles, as for instance disclosed in Pharmaceutical Dosage Forms, Disperse Systems, Volume 1, edited by H. A. Lieberman, M. M. Rieger, and G. S. Banker, 1988 by Marcel Dekker, New York and Basel.

DESCRIPTION OF THE INVENTION

The inventors have now surprisingly found that by using certain specific excipients, orally administrable liquid suspensions of ITF2357 are obtained, which are physically stable, chemically stable and palatable in the mouth, thus resulting in improved patient compliance. Suspensions are dispersed, two-phase systems, in which one phase ("internal" phase), the solid particles, is dispersed in the second phase ("continuous" or "external" phase), such as a liquid vehicle. As such, they are by definition thermodynamically unstable and tend to revert to an energetically more stable state by for example undergoing aggregation, sedimentation, crystal growth and caking. A suspension contains solid particles dispersed in a liquid or semisolid medium. As suspensions are thermodynamically unstable, the dispersed particles tend to aggregate and/or to sediment in order to reduce the surface area.

Particle size of the suspended particles influences sedimentation rate, particularly: a reduction of particle size leads to a decrease in the rate of sedimentation of the suspended particles, as explained by the Stokes' law:

$$V = \frac{d^2(\rho_1 - \rho_2)g}{18\eta}$$

where V is the velocity of sedimentation (cms), d is the diameter of the particle (cm), $\rho_1$ and $\rho_2$ are the densities of the suspended particles and medium or vehicle, g is the acceleration of gravity, and $\eta$ is the viscosity of the medium or vehicle. Processes such as milling and sieving can allow to achieve particle size reduction.

To minimise the settling of the dispersed particles and to prevent caking of sedimented particles the so-called "controlled flocculation" approach is most commonly used. In a flocculated suspension, the particles are loosely connected with each other to form floccules (or flocs), which are held together in a network-like structure. Flocculated particles are therefore weakly bonded. As such, they do not form a cake and are easily re-suspended. "Flocculating agents", such as electrolytes, surfactants, and polymers, can bring about flocculation.

Additional key factors to be considered when formulating a pharmaceutical suspension are the following:

The particles must have a low interfacial tension and must be easily wetted by the external phase. This is usually achieved by using surfactants.

The greater is the viscosity of the medium, the slower is the sedimentation (as per Stokes' law).

Nevertheless, which excipients will be successful in stabilizing a suspension is not predictable and their choice is critical to the physical and chemical stability of a suspension.

The inventors have surprisingly found that by using certain specific excipients orally administrable aqueous suspensions of Givinostat are obtained, which are physically and chemically stable. This is an essential requirement for industrial preparation and distribution of the pharmaceutical formulations.

More particularly, according to a first aspect, the present invention relates to aqueous suspensions comprising Givinostat and/or pharmaceutically acceptable salts and/or derivatives thereof, at least a wetting agent and/or at least a density-imparting agent.

Advantageously, the compositions of the present invention are chemically stable and palatable. With respect to tablets or capsules, they increase patient compliance when difficulties in swallowing arise.

A second aspect of the invention relates to said suspensions of Givinostat and/or pharmaceutically acceptable salts and/or derivatives thereof for use in the treatment of any disease responding to histone deacetylase inhibitors.

A third aspect of the invention relates to method(s) of preparation of said suspensions of Givinostat and/or pharmaceutically acceptable salts and/or derivatives thereof.

ITF2357 solubility in purified water is about 2.5 mg/mL. As expected, ITF2357 shows a pH-dependent solubility profile, with the lowest solubility at alkaline conditions. For example, solubility of ITF2357 in phosphate buffers at pH 2, 4.5, 6 and 8 is about 1.13-2.88-0.77 and 0.05 mg/mL respectively. Thus, it is technically possible to prepare aqueous solutions of ITF2357, having concentrations, e.g., between 0.02 and 0.3% w/v, intended for oral administration. However, because of the poor Givinostat solubility, large volume of an oral solution formulation would need to be administered to allow administration of effective drug doses and this pose patient compliance issues. Besides, in spite of its very good stability in the solid state, ITF2357 chemical stability decreases significantly when it is in solution. For example, solutions of ITF2357 in water and in phosphate buffer at pH values of 2, 4.5, 6 and 8, showed degradation of about 6.3%, 0.8%, 0.5% and 2.1% when stored for only 6 days at 40° C. In a preferred embodiment, the suspension according to the invention further comprising at least a buffering agent.

Preferably, the amount of Givinostat and/or pharmaceutically acceptable salts and/or derivatives thereof is comprised between 0.1% w/v and 20% w/v. In a preferred embodiment, Givinostat is present in amounts from 0.2% to 10% w/v, more preferably from 0.3% to 5%/0 w/v. Advantageously, the suspensions according to the invention are feasible in a wide range of Givinostat concentrations. This provides the doctors with different dosage and administration regimens, permits to personalize the treatment and, therefore, improves patient compliance. Preferably, the average particle size of Givinostat and/or pharmaceutically acceptable salts and/or derivatives thereof is lower than 200 μm (microns). In a more preferred embodiment, the average particle size is comprised between 100 μm and 1 μm, more preferably comprised between 50 μm and 5 μm.

According to a preferred embodiment of the invention, the wetting agent is at least one surfactant, preferably selected from: anionic surfactants, non-ionic surfactants and combinations thereof.

The amount of surfactant is critical to the quality of a suspension: too much of the surfactant may produce foam or deflocculated systems, both of which are undesirable; too low of the surfactant may not wet the solid particles properly, resulting in aggregation or clumps. Preferably, the wetting agent is present in amounts from 0.00025% to 2% w/v, preferably from 0.0005% to 0.5% w/v, more preferably from 0.001% to 0.2% w/v.

Suitable surfactants for the present invention may be selected from carboxylates, natural emulsifiers (e.g., phospholipids), esters of sulphuric acid (e.g., alkyl sulfates), sulfonates, non-ionic ethers (e.g., fatty alcohol ethoxylates, propoxylated alcohols, ethoxylated/propoxylated block polymers).

Preferably, the surfactant is selected from the group of non-ionic surfactants, belonging to the polyoxyethylene sorbitan fatty acid esters (e.g., polysorbates), polyoxyethylene fatty acids (e.g., polyoxyethylene stearates), polyoxyethylene alkyl ethers (or ethoxylated fatty alcohols), or poloxamers.

According to an embodiment, the non-ionic surfactant is selected from the group of polyoxyethylene sorbitan fatty acid esters, said non-ionic surfactant being preferably selected from:
Polyoxyethylene (20) sorbitan monolaurate, also known as Polysorbate 20, PEG(20) sorbitan monolaurate, or Tween 20, in amounts from 0.00025% to 2% w/v, preferably from 0.0005% to 0.5% w/v, more preferably from 0.001% to 0.2% w/v;
Polyoxyethylene (20) sorbitan monooleate, also known as Polysorbate 80, or PEG(20) sorbitan monooleate, or Tween 80, in amounts from 0.00025% to 2% w/v, preferably from 0.0005% to 0.5% w/v, more preferably from 0.001% to 0.2% w/v.

Preferably, the suspensions of the present invention further comprise a suspending agent.

The suspending agent may be any pharmaceutically acceptable viscosity-imparting agent, as taught in the scientific literature. They can be of natural, semi-synthetic or synthetic origin. Preferred suspending agents are selected from the group comprising inorganic clays, xanthan gum, agar-agar, alginates, tragacanth gum, Guar gum, and other natural gums, Cellulose derivatives (e.g., methylcellulose, hydroxyethylcellulose, hypromellose, carboxymethylcellulose, sodium carboxymethylcellulose), carbomers, maltodextrins, povidone, microcrystalline cellulose, and their combinations.

Preferably, tragacanth gum.

These suspending agents, alone or in combinations, are added in an amount enough to obtain a viscosity that is sufficiently high to retard sedimentation of the suspended particles but at the same time is not too high to make dispensing of the liquid dose difficult. Preferably, the suspending agent is present in amounts from 0.01% to 5% w/v, preferably from 0.05% to 2.0% w/v.

The suspending agents usually exhibit plastic, or pseudoplastic, or thixotropic flow or combinations thereof. This is instrumental to physical stability because they have relatively high viscosity under static conditions and therefore sedimentation is retarded, and flow easily at relatively high shear rates (for instance upon agitation), thus permitting easy dispensing from the bottle or vial containers. The viscosity of these systems may typically vary from about 10 milliPascalxsecond (mPa·s) to about 3,000 mPa sec., depending on the amount and physical grade of the suspending agents and the applied shear rate. However, the ease of resuspendability of the system upon gentle manual agitation and the no-caking effect even after prolonged period of storage is more important than the absolute viscosity.

The suspensions of the present invention may further include a preservative.

The preservative may be any pharmaceutically acceptable antimicrobial agent. Preferably, it is selected from the group comprising methylparaben, ethylparaben, propylparaben, butylparaben and/or sodium salts thereof, benzoic acid, sodium benzoate, sorbic acid, potassium sorbate, benzyl alcohol, phenylethanol, and mixtures thereof.

In a particularly preferred embodiment, the preservative is sodium benzoate.

The preservative is added in an amount enough to obtain an acceptable antimicrobial capacity. Preferably, it is in amounts from 0.05% to 2% w/v.

In a particularly preferred embodiment, the suspensions of the present invention include at least a density-imparting agent/sweetening agent. Such density-imparting agent is selected from sugars (e.g., sucrose, fructose, maltose) and polyhydric alcohols (e.g., mannitol, sorbitol, xylitol, dulcitol), also referred to as polyols or sugar alcohols.

Preferably, sucrose, sorbitol or mixture thereof. More preferably, sorbitol.

These excipients have a dual function. First, they increase the density of the medium (i.e., the external or continuous phase of the suspension), thereby retarding the rate of sedimentation of the suspended particles as per the Stokes' law:

$$V = \frac{d^2(\rho_1 - \rho_2)g}{18\eta}$$

Solid particles usually have a true density higher than that of pure water (1 g/mL). According to the equation above, the higher the density of the system medium (ρ2), the lower the sedimentation rate (V). Second, they improve palatability, due to their sweetness and good mouth-feel.

Advantageously, compositions of the invention containing for example, 40% w/v of sorbitol or 40% w/v of sucrose (example 2) surprisingly exhibit a high degree of chemical stability of Givinostat.

Preferably, in the suspensions according to the invention, the density-imparting agent is present in an amount from 5% w/v to 70% w/v, preferably from 10% w/v to 60% w/v, more preferably from 20% w/v to 50% w/v.

In a further preferred embodiment, the suspensions of the present invention further include at least a buffer agent for pharmaceutical use, inorganic or organic type, preferably selected from the group comprising phosphate buffer, citrate buffer, tartrate buffer and acetate buffer, suitable to buffer the pH of the suspension at a pH value comprised between 4 and 7, wherein Givinostat presents minimum solubility and/or maximum stability; preferably from 4 to 6.5, more preferably from 4.5 to 6.

Preferably the buffer agent used in the suspensions of the present invention is a tartrate or citrate buffer, more preferably a tartrate buffer. The tartrate or citrate buffer can be compounded in situ starting from tartaric or citric acid and sodium hydroxide or potassium hydroxide or a mixture thereof, or directly added as sodium tartrate or citrate or potassium tartrate or citrate or a mixture thereof.

The inventors have in fact surprisingly found out that Givinostat solubility at same pH is greatly influenced by the buffer type used as showed in example 3 where at same pH Givinostat resulted less soluble in tartrate buffer. Advantageously, a lower drug solubility is generally associated to a better chemical stability and palatability.

Preferably, in the suspensions according to the invention, the buffer agent is present in amount from 0.05% w/v to 5% w/v, preferably from 0.1% w/v to 2.5% w/v, more preferably from 0.5% w/v to 2% w/v.

A more preferred embodiment of the present invention relates to stable suspensions of Givinostat comprising at least a density imparting agent and a buffer system, preferably sorbitol or sucrose and tartrate buffer in modes and amounts previously described.

The inventors have surprisingly found that when certain specific excipients, such as density improving agents (e.g., Sorbitol or Sucrose) are included in the formulation, they not only influence active ingredient solubility, but also have a positive effect on chemical stability.

The inventors have surprisingly found that when specific excipients, such as buffering agents (e.g., phosphate, citrate, tartrate or acetate buffers), are included in the formulation, at the same formulation pH, the solubility of Givinostat is remarkably influenced. Surprisingly, Givinostat is remarkably less soluble when tartrate buffer is included in the formulation.

The examples 1, 6 and 9, shown below, demonstrate how suspensions of Givinostat containing sorbitol and tartrate buffer are both stable and palatable.

The suspensions of the present invention may also include at least one of the following excipients in amounts known by a skilled in the art:
 a flavouring agent;
 an "artificial" sweetening agent (e.g., saccharin, aspartame);
 a humectant/moistener, such as glycerol, polyethylene glycol, or propylene glycol;
 an anti-foam (e.g., Simethicone emulsion).

In another aspect, the present invention is directed to aqueous suspensions as described above for use in the treatment of diseases responding to histone deacetylase inhibitors, preferably psychiatric and neurological diseases (such as mood disorder, epilepsy, Alzheimer's disease), cancer (such as cutaneous T-cell lymphoma, Hodgkin's lymphoma, pancreatic cancer, multiple myeloma, cervical and ovarian cancer, breast cancer, lung cancer, prostate cancer, leukemia, myeloma, lymphoma), inflammatory diseases, HIV/AIDS, spinal muscular atrophy.

Preferably, for use in the treatment of diseases responding to Givinostat, more preferably selected from the group comprising systemic juvenile idiopathic arthritis, polycythemia vera, essential thrombocythemia, leukemia, myeloma, myelofibrosis, Duchenne muscular dystrophy, Becker muscular dystrophy and other forms of muscular dystrophies.

In a preferred embodiment, the suspensions according to the invention are administered to mammals, in particular humans, intended both as adult subject and as "pediatric population." The term "pediatric population" herein refers to that part of the population from birth to eighteen years.

Preferably, suspensions according to the invention are administered orally.

The suspensions according to the present invention can be prepared following any known process of the prior art. The present invention comprises therefore any method for manufacturing the suspensions of Givinostat of the present invention. In a particular embodiment, a suspension according to the present invention can be prepared according to the following steps:

A) Preparation of the Dispersing Vehicle
 (a) In a suitable vessel (e.g., jacketed stainless steel tank with stirrer), adding about 50-90% of the total available amount of purified water
 (b) Adding the prescribed amount of the density-imparting agent, either as solid or as a previously prepared aqueous solution at a suitable concentration). Maintaining under adequate stirring to ensure a homogeneous solution is obtained.
 (c) Adding the prescribed amount of suspending agent (if present) and, under stirring, giving the material the necessary time to hydrate, i.e., to uniformly disperse/dissolve to give a colloidal dispersion/solution, providing the required viscosity. This step is preferentially conducted under heating (e.g., 40-90° C.), in order to facilitate the hydration process. In addition, a moistening agent (e.g., glycerol) can be used to facilitate the dispersion of the suspending agent: an intimate and uniform mixture of the moistener and the suspending agent is first prepared, which is then added to the aqueous vehicle. This facilitates the hydration process, because the intimate mixture of the "rigid", high molecular weight polymer with the moistening agent (which is highly hydrophilic and water-soluble) exposes a hydrophilic surface to the aqueous vehicle.
 (d) Bringing the vehicle to room temperature (if necessary).
 According to an alternative embodiment, the order of addition of phase (b) and (c) can be inverted (i.e., the hydration of the suspending agent can be accomplished in purified water only and the density-imparting agent is then added to the hydrated suspending agent colloidal solution/dispersion).
 (e) Adding the prescribed amount of preservative system (if present) and keeping on stirring until complete solubilisation.
 (f) Adding the prescribed amounts the sweetening and flavouring agents (if present) and keeping on stirring until complete solubilisation.
 (g) Adding a previously prepared aqueous solution containing the buffer system (if present) and keeping on stirring until complete solubilisation.

According to an alternative embodiment:
the order of addition of phase (e), (f), and (g) can be changed;
the individual components of the buffer system can be added as solids and then solubilised under stirring;
the preservative system (if present) can be solubilised in step (a), (b), or (c); the sweetening and flavouring agents (if present) can be added after step (i), described below.

B) Pre-Dispersion (Wetting) of Givinostat (h) In a suitable container adding about 3-20% of the total available amount of purified water and dispersing under stirring the anti-foam agent (if present), then adding under stirring the wetting agent(s) and keeping on stirring until dissolved or thoroughly dispersed; then adding the prescribed amount of Givinostat and/or pharmaceutically acceptable salts and/or derivatives thereof and stirring until a homogeneous, lump-free slurry is obtained.

C) Preparation of the Final Bulk Suspension (i) Adding the Givinostat pre-dispersion to the dispersing vehicle, under vigorous stirring, and keeping on stirring until a homogeneous dispersion is obtained:
(j) Checking pH and, if necessary, adjusting it to the 4-7 range with Tartaric Acid or Sodium Hydroxide; preferably from 4 to 6.5, more preferable from 4.5 to 6.
(k) Adding purified water q.s. to final volume and stirring:
(l) Homogenizing the final suspension through a suitable homogenizer (e.g., colloid mill, piston-type, ultraturrax-type, etc.);
(m) Distributing the prescribed volume of suspension into individual primary containers (e.g., glass or plastic bottles) and cap.

According to an alternative embodiment, the whole vehicle can be prepared (i.e., the aqueous vehicle containing all components except Givinostat) and the active ingredient then added slowly to the vehicle, under stirring.

Possible pharmaceutical suspensions of the invention are provided in the attached examples, which, however, are only intended to illustrate and not to limit the invention.

EXAMPLES

The suspensions according to the invention were prepared as reported above, using an ultraturrax-type homogenizer.

The physical stability of the suspensions was verified by the following techniques: appearance (by visual inspection); optical microscopy (to determine particle size distribution and verify whether or not crystal growth would occur); resuspendability (by manual shaking). The chemical stability of Givinostat suspensions was assessed by means of a specific and stability indicating HPLC method.

Example 1: Oral Suspension—Givinostat 10 mg/mL or 1% w/v, pH 6

| Ingredient | Quantity (mg) | Quantity (% w/v) |
|---|---|---|
| Givinostat | 10 | 1 |
| Sodium benzoate | 4.4 | 0.44 |
| Flavouring agents | 2 | 0.2 |
| Saccharin Sodium | 1 | 0.1 |
| Sorbitol | 400 | 40 |
| Glycerol | 25 | 2.5 |
| Tragacanth gum | 3.0 | 0.3 |
| Polysorbate 20 | 0.016 | 0.0016 |
| Tartaric acid | 6.5 (*) | 0.65 (*) |
| Sodium hydroxide | 3.5 (*) | 0.35 (*) |
| Purified water | qb to 1 mL | qs to 100 mL | q.s. = quantum satix
(*) tartrate buffer. The pH is adjusted to 6 during manufacturing with further tartaric acid and/or sodium hydroxide as necessary Manufacturing Method:

(a) Putting about 50-90% of the total available amount of purified water into a suitable jacketed stainless steel tank with stirrer and heating to about 70°÷90° C. Adding the prescribed amount of Sorbitol as "Liquid Sorbitol" (commercially available 70% solution) and maintaining under adequate stirring until the solution reaches the temperature of about 70°÷+90.
(b) While maintaining the temperature at 70°÷90° C., adding under stirring Tragacanth gum, previously intimately dispersed in the prescribed amount of Glycerol. Let the gum hydrate, until a homogeneous system is obtained.
(c) Cooling down the hydrated vehicle to room temperature (20÷30° C.) under stirring.
(d) Adding the prescribed amount of Sodium benzoate into the tank, under stirring, then adding the prescribed amounts of Saccharin sodium and keeping on stirring.
(e) In a separate suitable container, preparing a solution of the prescribed amounts of Tartaric acid and Sodium hydroxide in purified water, and then adding this solution to the tank, under stirring.
(f) Finally, adding the prescribed amounts of the flavouring agents, under stirring. Checking and adjusting pH of vehicle if necessary with further Tartaric acid and/or Sodium hydroxide previously dissolved in purified water.
(g) In a separate suitable container, preparing the pre-dispersion of Givinostat: in about 3-20% of the total available amount of purified water, adding under stirring the prescribed amount of Polysorbate 20, until dissolved, and then adding the prescribed amount of Givinostat, under stirring. Keeping on stirring until homogeneous, lump-free slurry is obtained.
(h) Adding Givinostat pre-dispersion to the vehicle, under vigorous stirring, and keeping on stirring until a homogeneous dispersion is obtained.
(i) Checking and adjusting pH of suspension if necessary with further Tartaric acid and/or Sodium hydroxide previously dissolved in purified water.
(j) Adding purified water q.s. to final volume and stirring.
(k) Homogenizing the final suspension through a high-shear homogenizer, by eventually re-circulating the suspension and/or transferring it into a suitable storage container, passing the whole suspension through the homogenizer.
(l) By maintaining the final bulk suspension under stirring, distributing into glass or plastic bottle, for example 150 mL nominal capacity amber PET (Poly Ethylene Terephthalate) bottles, by means of a suitable filling machine (filling volume for example 120 mL/bottle) and sealing the bottles with childproof tamper resistant screw caps, for example in HDPE (High Density Poly Ethylene) or PP (polyethylene) with a LDPE (Low Density Poly Ethylene) shutter.

Stability:

this formulation proved to be chemically and physically very stable, even after 6-month storage at 40° C./75% RH (relative humidity): HPLC assay did not change significantly remaining well within ±5% from theoretical value, related substances increased in a negligible way remaining below a limit value of 1%, pH diminished in a negligible way remaining within ±0.5 unit from theoretical value, appearance and resuspendability were practically unchanged, and optical microscopy evaluation did not reveal any particle growth, as shown in Table 1.

TABLE 1

|  | Time zero | 1 month | 3 months | 6 months |
|---|---|---|---|---|
| Appearance/ Resuspendability | White to off-white or faintly pink, homogeneous suspension when mixed | | White to off-white or faintly pink, homogeneous suspension when mixed | |
| Givinostat assay (HPLC, % of label) | 101.3 | 100.6 | 100.4 | 99.2 |
| Total related substances (HPLC, area %) | 0.4 | 0.6 | 0.6 | 0.7 |
| pH | 5.9 | 5.8 | 5.7 | 5.6 |
| Particle size % < 100 μm (Optical % < 50 μm microscopy) | 98 91 | 100 91 | 97 92 | 99 98 |

This formulation could be prepared both at laboratory scale (scale≤5 L) and at industrial scale (scale >100 L), thus demonstrating that the suspensions of the present invention can be industrialized.

Givinostat suspension physically and chemically stable can be prepared according to the composition and method of preparation described in example 1 and containing from 0.1 to 20% w/v of Givinostat. The amount of Polysorbate 20 may be increased or diminished in the range from about 0.00025% to about 2% w/v as necessary in order to obtain a complete wetting of the active principle.

Example 2

During formulation development studies, different density-imparting agents were used, selected from the group of "sugar alcohols" and saccharides, such as Sorbitol and Sucrose.

Sorbitol is also a sugar alcohol. Its IUPAC name is (2S,3R,4R,5R)-Hexane-1,2,3,4,5,6-hexol. Molecular formula is C6H14O6. Chemical structure is reported below.

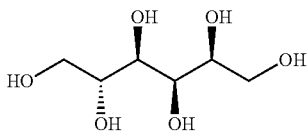 [SMILES: OC[C@@H](O)[C@@H](O)[C@H](O)[C@@H](O)CO]

Sorbitol is very soluble in water (solubility is about 2.2 g/mL).

Sucrose, also called saccharose, is a white, odorless, crystalline powder with a sweet taste. It is a disaccharide with a molecule of Glucose and a molecule of Fructose bonded together with a glycosidic linkage. Molecular formula is C12H22O11. Chemical structure is reported below.

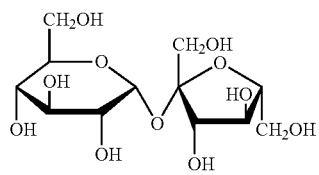

It is very soluble in water (i part dissolves in 0.3 parts of water at 20° C.).

Thus, they are commonly used in syrups and oral suspensions as sweetening and density-imparting agents.

Solubility of Givinostat was tested in aqueous vehicles at pH 6, containing Phosphate buffer. Tween 20 as wetting agent and either Sorbitol or Sucrose (40% w/v). To this aim, an amount of Givinostat sufficient to ensure saturation was mixed with 15 mL of each vehicle in separate vials. These vials were shaken at 25° C.±PC for at least 24 hours in order to obtain equilibrium. The saturated solution was then separated from the excess solid by filtration and Givinostat (ITF2357) was quantitated in the filtrate by UV-Vis spectrophotometric technique. Solubility values are summarized in Table 2.

TABLE 2

| Aqueous vehicle | ITF2357 Solubility (mg/mL) |
|---|---|
| Phosphate buffer pH 6, Tween 20, Sorbitol 10% (w/v) | 2.341 |
| Phosphate buffer pH 6, Tween 20, Sorbitol 20% (w/v) | 2.106 |
| Phosphate buffer pH 6, Tween 20, Sorbitol 30% (w/v) | 2.018 |
| Phosphate buffer pH 6, Tween 20, Sorbitol 40% (w/v) | 1.929 |
| Phosphate buffer pH 6, Tween 20, Sucrose 40% (w/v) | 3.875 |

Surprisingly, ITF2357 solubility decreases when Sorbitol concentration is increased. This is unexpected, because a polyalcohol can often be used to increase the solubility of a drug and this effect is concentration-dependent, i.e., the higher the polyalcohol amount, the higher the solubilising effect.

Also surprising is the fact that the Sucrose exerts a more significant solubilising effect compared to the Sorbitol.

An accelerated chemical stability study was performed on 1% (w/v) ITF2357 suspensions containing either Sorbitol or Sucrose (40% w/v). Results, expressed as HPLC Total Impurities (%) were surprising too, as reported in Table 3.

TABLE 3

| 1% (w/v) ITF2357 | % Total Impurities (HPLC) after | |
|---|---|---|
| Suspension containing | 4 days at 5° C. (*) | 4 days at 80° C. |
| 40% (w/v) Sorbitol | 0.48 | 1.71 |
| 40% (w/v) Sucrose | 0.46 | 2.21 |

(*) taken as initial time result

The inventors have surprisingly found that when certain specific excipients, such as density improving agents (e.g., Sorbitol or Sucrose) are included in the formulation, they not only influence active ingredient solubility, but also have a positive effect on chemical stability.

Example 3

During formulation studies, solubility of ITF2357 was determined in different buffers, selected from the group of the inorganic (phosphate) and organic (acetate and tartrate) buffer.

In table 4 solubility value determined on ITF 2357 saturated solution in different buffer at pH 4.5 are reported.

TABLE 4

| Aqueous vehicle | ITF2357 solubility (mg/mL) (*) |
|---|---|
| Phosphate buffer pH 4.5 | 2.88 |
| Acetate buffer pH 4.5 | 5.10 |
| Tartrate buffer pH 4.5 | 0.23 |

(*) values rounded to the second decimal digit

Surprisingly at same pH solubility is greatly influenced by the buffer type. Givinostat resulted less soluble in Tartrate buffer. This is truly susrprising as generally organic buffer can exercise a complexing co-solubilizing effect while in this specific case tartrate buffer not only does not exercise such effect but on the contrary is limiting ITF2357 solubility.

Solubility of ITF2357 determined in suspension vehicles having compositions as described in Example 1, thus containing Sorbitol at 40% w/v and Tartrate buffer, at different pH (pH range from 4 to 7 adjusted with Tartaric Acid or Sodium Hydroxide) are shown in Table 5.

TABLE 5

| Vehicle | ITF2357 solubility (mg/mL) |
|---|---|
| Tartrate buffer pH = 4.0, Tween 20, Sorbitol 40% w/v | 0.21 |
| Tartrate buffer pH = 5.0, Tween 20, Sorbitol 40% w/v | 0.15 |
| Tartrate buffer pH = 5.5, Tween 20, Sorbitol 40% w/v | 0.16 |
| Tartrate buffer pH = 6.0, Tween 20, Sorbitol 40% w/v | 0.15 |
| Tartrate buffer pH = 6.5, Tween 20, Sorbitol 40% w/v | 0.16 |
| Tartrate buffer pH = 7.0, Tween 20, Sorbitol 40% w/v | 0.15 |

Surprisingly the use of specific excipients, such as buffering agents (in particular tartrate buffer), wetting agents and densifying agents (in particular sorbitol) in the formulation according to the invention decreases the solubility of Givinostat.

This represents a remarkable advantage as a lower drug solubility is generally associated to a better chemical stability and palatability.

Example 4: Oral Suspension—Givinostat 10 mg/mL or 1.0% (w/v)

| Ingredient | Quantity (mg) |
|---|---|
| Givinostat | 10 |
| Methyl paraben | 1.35 |
| Propyl paraben | 0.15 |
| Sucrose | 400 |
| Glycerol | 25 |
| Tragacanth gum | 3.0 |
| Polysorbate 80 | 0.063 |
| Purified water | q.s. to 1 mL |

Stability:

this formulation proved to be stable for at least 1 week at 40° C.

Givinostat suspension physically and chemically stable can be prepared according to the composition described in example 4 and containing from 0.2 to 10% w/v of Givinostat. The amount of Polysorbate 80 may be increased or diminished in the range from about 0.0005% to about 1% w/v as necessary in order to obtain a complete wetting of the active principle.

Example 5: Oral Suspension—Givinostat 10 mg/mL or 1.0% (w/v)

| Ingredient | Quantity (mg) |
|---|---|
| Givinostat | 10 |
| Methyl paraben | 1.35 |
| Propyl paraben | 0.15 |
| Sucrose | 400 |
| Glycerol | 25 |
| Tragacanth gum | 3.0 |
| Polysorbate 20 | 0.063 |
| Purified water | q.s. to 1 mL |

Stability:

this formulation proved to be stable for at least 1 week at 40° C.

Givinostat suspension physically and chemically stable can be prepared according to the composition described in example 4 and containing from 0.2 to 10% w/v of Givinostat. The amount of Polysorbate 20 may be increased or diminished in the range from about 0.0005% to about 1% w/v as necessary in order to obtain a complete wetting of the active principle.

Example 6: Oral Suspension—Givinostat 10 mg/mL or 1% w/v, pH 5

| Ingredient | Quantity (mg) | Quantity (% w/v) |
|---|---|---|
| Givinostat | 10 | 1 |
| Sodium benzoate | 4.4 | 0.44 |
| Flavouring agents | 2 | 0.2 |
| Saccharin Sodium | 1 | 0.1 |
| Sorbitol | 400 | 40 |
| Glycerol | 25 | 2.5 |
| Tragacanth gum | 3.0 | 0.3 |
| Polysorbate 20 | 0.016 | 0.0016 |
| Tartaric acid | 6.5 (*) | 0.65 (*) |
| Sodium hydroxide | 3.25 (*) | 0.325 (*) |
| Purified water | q.s. to 1 mL | q.s. to 100 mL | q.s. = quantum satix
(*) tartrate buffer. The pH is adjusted to 5 during manufacturing with further tartaric acid and/or sodium hydroxide as necessary Manufacturing Method:

a described in example 1.

Stability:

this formulation proved to be chemically and physically very stable, even after 6-month storage at 40° C./75% RH (relative humidity): HPLC assay did not change significantly remaining well within ±5% from theoretical value, related substances increased in a negligible way remaining below a limit value of 1%, pH diminished in a negligible way remaining within ±0.5 unit from theoretical value, appearance and resuspendability were practically unchanged, and optical microscopy evaluation did not reveal any particle growth, as shown in Table 6.

TABLE 6

| | Time zero | 1 month | 3 months | 6 months |
|---|---|---|---|---|
| Appearance/ Resuspendability | White to off-white or faintly pink, homogeneous suspension when mixed | | White to off-white or faintly pink, homogeneous suspension when mixed | |
| Givinostat assay (HPLC, % of label) | 98.1 | 98.7 | 99.1 | 102.4 |
| Total related substances (HPLC, area %) | 0.23 | 0.29 | 0.32 | 0.38 |
| pH | 4.99 | 4.89 | 5.02 | 4.85 |
| Particle size % < 100 μm (Optical microscopy) | 100 | 100 | 100 | 100 |
| % < 50 μm | 99 | 100 | 99 | 98 |

This formulation could be prepared both at laboratory scale (scale ≤5 L) and at industrial scale (scale >100 L), thus demonstrating that the suspensions of the present invention can be industrialized.

Givinostat suspension physically and chemically stable can be prepared according to the composition and method of preparation described in example 6 and containing from 0.3 to 5% w/v of Givinostat. The amount of Polysorbate 20 may be increased or diminished in the range from about 0.0005% to about 0.5% w/v as necessary in order to obtain a complete wetting of the active principle.

Example 7: Oral Suspension—Givinostat 10 mg/mL or 1% w/v, pH 4.5

| Ingredient | Quantity (mg) | Quantity (% w/v) |
|---|---|---|
| Givinostat | 10 | 1 |
| Sodium benzoate | 4.4 | 0.44 |
| Flavouring agents | 2 | 0.2 |
| Saccharin Sodium | 1 | 0.1 |
| Sorbitol | 400 | 40 |
| Glycerol | 25 | 2.5 |
| Tragacanth gum | 3.0 | 0.3 |
| Polysorbate 20 | 0.016 | 0.0016 |
| Tartaric acid | 6.5 (*) | 0.65 (*) |
| Sodium hydroxide | 3.25 (*) | 0.325 (*) |
| Purified water | q.s. to 1 mL | q.s. to 100 mL | q.s. = quantum satix
(*) tartrate buffer. The pH is adjusted to 4.5 during manufacturing with further tartaric acid and/or sodium hydroxide as necessary Manufacturing Method:
a described in example 1.
Stability:
this formulation proved to be chemically and physically very stable, even after 1-month storage at 55° C.: HPLC assay did not change significantly, pH did not change significantly, appearance and resuspendability were practically unchanged.

Example 8: Oral Suspension—Givinostat 10 mg/mL or 1% w/v, pH 5.5

| Ingredient | Quantity (mg) | Quantity (% w/v) |
|---|---|---|
| Givinostat | 10 | 1 |
| Sodium benzoate | 4.4 | 0.44 |
| Flavouring agents | 2 | 0.2 |
| Saccharin Sodium | 1 | 0.1 |
| Sorbitol | 400 | 40 |
| Glycerol | 25 | 2.5 |
| Tragacanth gum | 3.0 | 0.3 |
| Polysorbate 20 | 0.016 | 0.0016 |
| Tartaric acid | 6.5 (*) | 0.65 (*) |
| Sodium hydroxide | 3.25 (*) | 0.325 (*) |
| Purified water | q.s. to 1 m.L | q.s. to 100 mL | q.s. = quantum satix
(*) tartrate buffer. The pH is adjusted to 5.5 during manufacturing with further tartaric acid and/or sodium hydroxide as necessary Manufacturing Method:
a described in example 1.
Stability:
this formulation proved to be chemically and physically very stable, even after 1-month storage at 55° C.: HPLC assay did not change significantly, pH did not change significantly, appearance and resuspendability were practically unchanged.

Example 9: Evaluation of Palatability of Givinostat Suspensions According to the Invention Vs. Givinostat Solutions The palatability of Givinostat suspensions according to the invention (composition as in example 1 and example 6) and referred for the purpose of this palatability study formulations A and B, was evaluated in comparison to:
- suspensions according to the invention having similar composition to formulations A and B but whereas the tartrate buffer was replaced with phosphate buffer, named for the purpose of this palatability study formulations C and D
- suspensions according to the invention having similar composition to formulations A and B but whereas the Sorbitol was replaced with an additional amount of Saccharin Sodium such as to compensate its sweetening power (Sorbitol has a sweetening power of approximately 0.6 times that of Sucrose, Saccharin Sodium has a sweetening power of about 450 times that of Sucrose, therefore the sweetening power of a 40% w/v Sorbitol concentration was compensated by an increase of the Saccharin Sodium concentration of 0.055% w/v), named for the purpose of this palatability study formulations E and F.
- Givinostat comparative solutions in phosphate buffer at pH 5 and 6 and containing the same concentration of Saccharin Sodium present in formulations E and F (thus having equivalent sweetening power of previous formulations), prepared at about the maximum Givinostat concentration that can be formulated as a solution of about 2 mg/mL (0.2% w/v), named for the purpose of this palatability study formulations G and H.

Samples of each formulation were evaluated blindly by three researchers (referred to herein as the "Panelists") according to the following protocol:
- the samples were prepared by an independent researcher, in same dark glass bottles and anonymously (bottle only identified by alphabetic letter corresponding to the formulation prepared, therefore the panelists could not know the sample that they were required to taste);
- each panelist received 5 mL of each formulation randomly. The volume administered was kept and swished in the mouth for about 5 seconds, then expelled from the mouth. Panelists were not allowed to rinse the mouth with spring water for at least 5 minutes after expelling the sample;

a wash-out period of at least 2 hour was kept between a taste test and the next;

not more than 4 samples per day were tasted and evaluated by each panelist;

an initial assessment was required to the panelist immediately after the administration, based on a general "mouth feeling", in particular the panelists were asked to express their opinion about:

perception of sweet/bitter taste (using the following arbitrary scale: 0=very sweet, 1=sweet, 2=slightly sweet, 3=not distinguishable between slightly sweet and slightly bitter, 4=slightly bitter, 5=bitter, 6-=very bitter)

feeling of pleasantness (using the following arbitrary scale: 0=very good, 1=good, 2=acceptable 3=not distinguishable between acceptable and not good, 4=not good, 5=bad, 6=very bad)

a second assessment was required to the panelist after 5' from administration, based on a general "mouth feeling", relative to the aftertaste (using the following arbitrary scale: 0=very sweet, 1=sweet, 2=slightly sweet, 3=not distinguishable between slightly sweet and slightly bitter, 4=slightly bitter, 5=bitter, 6=very bitter)

Results can be summarized as follows:

Givinostat suspensions 1% w/v having compositions as in examples 1 and 6 (named formulations A and B)
  perception of sweet/bitter taste: rating from 1 to 2 (sweet or slightly sweet)
  pleasantness: rating from 1 to 2 (good or acceptable)
  aftertaste: rating from 2 to 3 (slightly sweet or not distinguishable between slightly sweet and slightly bitter)

Givinostat suspensions 1% w/v having compositions as in examples 1 and 6 whereas the tartrate buffer was replaced with phosphate buffer (named formulations C and D)
  perception of sweet/bitter taste: rating from 2 to 3 (slightly sweet or not distinguishable between slightly sweet and slightly bitter)
  pleasantness: rating from 2 to 3 (acceptable or not distinguishable between acceptable and not good)
  aftertaste: rating from 3 to 4 (not distinguishable between slightly sweet and slightly bitter or slightly bitter)

Givinostat suspensions 1% w/v having compositions as in examples 1 and 6 whereas whereas the Sorbitol was replaced with an additional amount of Saccharin Sodium such as to compensate its sweetening power (named formulations E and F)
  perception of sweet/bitter taste: rating from 2 to 3 (slightly sweet or not distinguishable between slightly sweet and slightly bitter)
  pleasantness: rating from 2 to 3 (acceptable or not distinguishable between acceptable and not good)
  aftertaste: rating from 3 to 4 (not distinguishable between slightly sweet and slightly bitter or slightly bitter)

Givinostat solutions 0.2% w/v (named formulations G and H)
  perception of sweet/bitter taste: rating from 4 to 5 (slightly bitter or bitter)
  pleasantness: rating from 4 to 5 (not good or bad)
  aftertaste: rating from 5 to 6 (bitter or very bitter)

In all cases the results show a favorable profile of palatability for suspensions according to the invention when compared to the solutions (G and H) in spite of the fact that the latter, having same sweetening power, contain a lower concentration of active principle.

In particular, the suspensions containing both Sorbitol and Tartrate buffer (A and B) have a particularly favourable palatability profile, as well as an excellent stability as described above. The suspensions of the present invention are therefore physically and chemically stable and palatable, with this representing a significant improvement in the art, in particular in allowing the oral administration of Givinostat in a liquid dosage form for the treatment of any disease responsive to inhibitors of histone deacetylases, and in particular responsive to Givinostat, in all those patients having problems with swallowing of solid pharmaceutical forms such as capsules or tablets, such as for example elderly or pediatric or undergoing chemotherapy regimen patients, but not limited to them.

The invention claimed is:

1. An aqueous suspension comprising Givinostat and/or a pharmaceutically acceptable salt thereof, a wetting agent, a density-imparting agent, a buffering agent, and a suspending agent; wherein the wetting agent is a polyoxyethylene sorbitan fatty acid ester, poloxamer, or a mixture thereof, the density-imparting agent is sorbitol, sucrose or a mixture thereof, and the buffering agent is a phosphate buffer, citrate buffer, or tartrate buffer, and the suspending agent is tragacanth gum or xanthan gum.

2. The suspension according to claim 1, characterized in that Givinostat and/or a pharmaceutically acceptable salt thereof is present in amounts between 0.1% w/v and 20% w/v.

3. The suspension according to claim 1, characterized in that Givinostat and/or pharmaceutically acceptable salt thereof is present in particle form having an average particle size lower than 200 μm.

4. The suspension according to claim 1, characterized in that said wetting agent is a polyoxyethylene sorbitan fatty acid ester.

5. The suspension according to claim 1, characterized in that said wetting agent is present in amounts between 0.00025% w/v and 2% w/v.

6. The suspension according to claim 1, characterized in that said density-imparting agent is present in amounts between 5% w/v and 70% w/v.

7. The suspension according to claim 1, characterized in that said buffering agent is tartrate buffer.

8. The suspension according to claim 1, characterized in that said buffering agent is present in amounts between 0.05% w/v and 5% w/v.

9. The suspension according to claim 1, characterized in that said suspending agent is present in amounts between 0.01% w/v and 5% w/v.

10. The suspension according to claim 1, characterized in that said suspending agent is tragacanth gum.

11. A method for treating a disease responding to histone deacetylase inhibitors selected from the group consisting of: neurological and psychiatric diseases, cancer, inflammatory diseases, HIV/AIDS, and spinal muscular atrophy; comprising the step of administering the suspension according to claim 1 to a subject in need thereof.

12. The method according to claim 11, which treats disease responding to Givinostat selected from the group consisting of systemic juvenile idiopathic arthritis, polycythaemia vera, essential thrombocythemia, leukemias, myelomas, myelofibrosis, Duchenne muscular dystrophy, Becker muscular dystrophy and other forms of muscular dystrophy.

13. The method according to claim 12, characterized in that it is administered orally.

14. A method for preparing the suspension according to claim 1, comprising the steps of:
    a) preparing a dispersing vehicle comprising water, the density-imparting agent, the suspending agent and the buffering agent;
    b) pre-dispersing Givinostat into an aqueous solution comprising the wetting agent; and
    c) adding said pre-dispersion to said dispersing vehicle in order to obtain a suspension.

15. The suspension according to claim 1, characterized in that said polyoxyethylene sorbitan fatty acid ester is polysorbate 20 or polysorbate 80.

16. The suspension according to claim 1, characterized in that said density-imparting agent is sorbitol.

17. The suspension according to claim 1, wherein the wetting agent is a polyoxyethylene sorbitan fatty acid ester, the density-imparting agent is sorbitol, the buffer agent is a tartrate buffer, and the suspending agent is tragacanth gum.

* * * * *

UNITED STATES PATENT AND TRADEMARK OFFICE
CERTIFICATE OF CORRECTION

PATENT NO. : 10,688,047 B2
APPLICATION NO. : 15/770443
DATED : June 23, 2020
INVENTOR(S) : Giuseppe Colombo et al.

Page 1 of 1

It is certified that error appears in the above-identified patent and that said Letters Patent is hereby corrected as shown below:

On the Title Page

Column 2, "Other Publications", Line 4: PCT/162016/056496 should read PCT/IB2016/056496.

Signed and Sealed this
Twenty-fifth Day of August, 2020

Andrei Iancu
*Director of the United States Patent and Trademark Office*